United States Patent
Dafinger et al.

(10) Patent No.: US 8,765,995 B2
(45) Date of Patent: Jul. 1, 2014

(54) PROCESS AND APPARATUS FOR PREPARING VINYL ACETATE MONOMER

(75) Inventors: Willibald Dafinger, Röhrnbach (DE); Peter Holl, Emmerting (DE); Günther Rudolf, Mühldorf (DE); Martin Schönleben, Reut (DE)

(73) Assignee: Wacker Chemie AG, Munich (DE)

( * ) Notice: Subject to any disclaimer, the term of this patent is extended or adjusted under 35 U.S.C. 154(b) by 413 days.

(21) Appl. No.: 13/202,227

(22) PCT Filed: Feb. 16, 2010

(86) PCT No.: PCT/EP2010/051878
§ 371 (c)(1),
(2), (4) Date: Oct. 5, 2011

(87) PCT Pub. No.: WO2010/094660
PCT Pub. Date: Aug. 26, 2010

(65) Prior Publication Data
US 2012/0041231 A1    Feb. 16, 2012

(30) Foreign Application Priority Data
Feb. 19, 2009   (DE) .......................... 10 2009 001 021

(51) Int. Cl.
*C07C 67/05*    (2006.01)
(52) U.S. Cl.
CPC ..................................... *C07C 67/05* (2013.01)
USPC .......................................... 560/248; 560/261
(58) Field of Classification Search
None
See application file for complete search history.

(56) References Cited

U.S. PATENT DOCUMENTS

| | | | |
|---|---|---|---|
| 5,739,391 | A | 4/1998 | Ruppel et al. |
| 6,849,243 | B1 | 2/2005 | Hagemeyer et al. |
| 7,226,567 | B1 | 6/2007 | Olbert et al. |
| 2008/0300414 | A1 | 12/2008 | Schliephake et al. |
| 2009/0054683 | A1 | 2/2009 | Bueker et al. |

FOREIGN PATENT DOCUMENTS

| | | |
|---|---|---|
| DE | 4431949 | 3/1995 |
| DE | 19914066 | 10/2000 |
| DE | 102007025869 | 7/2008 |
| EP | 1033167 | 9/2000 |
| WO | 0054877 | 9/2000 |
| WO | 2006042659 | 4/2006 |

OTHER PUBLICATIONS

International Search Report for PCT/EP2010/051878 dated Jul. 23, 2010.
International Preliminary Report on Patentability for PCT/EP2010/051878 dated Apr. 1, 2011.
Jeong-Bin Lee, et al., "Development of MATLAB/Simulink-based Dynamic Simulator for Vinyl Acetate Monomer Process", Theories and Applications of Chem. Eng., 2007, vol. 13, No. 2, pp. 1472-1475; Bibliographic English language abstract of Jeong-Bin Lee, et al.
Korean Office Action, 3 pages (2012).
Reporting letter dated Jan. 11, 2013, from Korean associates including a summary of the Office Action.

*Primary Examiner* — Michael Barker
(74) *Attorney, Agent, or Firm* — RatnerPrestia

(57) ABSTRACT

The invention provides a process for preparing vinyl acetate monomer (VAM) by reacting ethylene with acetic acid and oxygen in a tube bundle reactor in a heterogeneously catalysed, continuous gas phase process, characterized in that a high-performance catalyst with a space-time yield of more than 700 g of VAM/l of catalyst×hour is used for catalysis, and in that the tube bundle reactor comprises tubes with a ratio of inner surface area to volume of $\geq 130$ m$^{-1}$.

8 Claims, 4 Drawing Sheets

PROCESS AND APPARATUS FOR PREPARING VINYL ACETATE MONOMER

CROSS REFERENCE TO RELATED APPLICATIONS

This application is the national phase filing of international patent application No. PCT/EP2010/051878, filed 16 Feb. 2010, and claims priority of German patent application number 10 2009 001 021.1, filed 19 Feb. 2009, the entireties of which applications are incorporated herein by reference.

FIELD OF THE INVENTION

The invention relates to a process and an apparatus for preparing vinyl acetate monomer in a heterogeneously catalysed, continuous gas phase process by reacting ethylene with acetic acid and oxygen in a tube bundle reactor.

BACKGROUND OF THE INVENTION

Vinyl acetate monomer (VAM) is prepared in a continuous process with recycling of the purified product stream (cycle gas system). In a heterogeneously catalysed gas phase process, ethylene reacts with acetic acid and oxygen over fixed bed catalysts which generally comprise palladium and alkali metal salts on a support material and may additionally be doped with gold, rhodium or cadmium.

The ethylene, oxygen and acetic acid reactants are reacted in an exothermic reaction (VAM: $\Delta_B H°_{299}$=−176 kJ/mol), generally at a pressure of 1 to 30 bar and a temperature of 130° C. to 200° C., in a fixed bed tubular reactor to give vinyl acetate monomer:

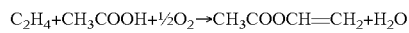

The main side reaction is the total oxidation of ethylene to $CO_2$:

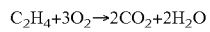

The heat of formation here is $A_B H°_{299}$=−1324 kJ/mol!

The ethylene conversion is about 10%, the acetic acid conversion 20 to 30%, and the oxygen conversion up to 90%.

In the preparation of vinyl acetate monomer, a gas mixture consisting predominantly of ethylene, carbon dioxide, ethane, nitrogen and oxygen is circulated. Upstream of the fixed bed tubular reactor, the gas stream is admixed with the acetic acid, ethylene and oxygen reactants, and brought to reaction temperature with steam-operated heat exchangers. The cycle gas is enriched with acetic acid typically by means of a steam-heated acetic acid saturator or acetic acid evaporator.

After the reaction, the reaction products and unconverted acetic acid are condensed out of the cycle gas and sent to workup. Uncondensed product is scrubbed out in a scrubber operated with acetic acid. The cycle gas or a portion thereof, before being admixed again with the reactants, is purified to free it of carbon dioxide formed. The condensed vinyl acetate monomer and water products, and also unconverted acetic acid, are separated from one another in a multistage distillation process typically operated with steam. The customary distillation steps are dewatering (optionally also preliminary dewatering), azeotropic distillation, pure VAM column, residue workup, and low boiler and high boiler removal.

The reaction temperature in the fixed bed tube bundle reactor, generally from 130° C. to 200° C., is set by means of evaporative water cooling at a pressure of 1 to 10 bar. This forms steam, known as in-process steam, generally at a temperature of 120° C. to 185° C., at a pressure of 1 to 10 bar, preferably 2.5 to 5 bar. The decline in activity over the operating time of a catalyst is balanced by increasing the reaction temperature, i.e. the operating pressure of the evaporative water cooling. To conserve the catalyst, for the purpose of achieving a maximum service life, and to optimize the ethylene selectivity, by minimizing the $CO_2$ formation, the vinyl acetate reaction should be conducted for as long as possible with as low as possible a reaction temperature.

In general, the fixed bed tube bundle reactors are formed from several thousand, typically 2000 to 6000, tightly packed and vertically arranged, cylindrical tubes. For industrial scale use, tubes with a length of 5 to 6 m and an internal diameter of 33 mm to 40 mm are used for this purpose. The surface/volume ratio is generally 100 to 120 m$^{-1}$.

A problem in vinyl acetate monomer preparation in a heterogeneously catalysed gas phase process, especially given increasingly high-performance catalysts, is the heat of reaction released. This is because the process is characterized by significant exothermicity, to a lesser degree in the main reaction than in the side reaction of ethylene oxidation. Even given good ethylene selectivity values (>92%), at a molar ratio of VAM: $CO_2$ of approx. 7:1, owing to the high heat of formation of the $CO_2$, half of the heat of reaction originates from this side reaction! Even given the constant improvement in VAM catalysts with regard to the space-time yield (STY), it is therefore never possible at the same time also to improve the ethylene selectivity $S_E$ in such a way that, as a result of the increase in STY, the overall exothermicity would also be reduced.

The procedure in the prior art to date has been to compress to a higher degree with higher-performance cycle gas compressors, in order that the flow rate of the cycle gas was increased, and the axial heat removal was optimized. Disadvantages are the higher pressure differences in all cycle gas apparatuses, and the difficulty of controlling the high gas velocity of the cycle gas. For the conventional VAM catalysts, the STY of which is between 400 and 700 g of VAM/l of catalyst×h, such measures, with all the disadvantages mentioned, were sufficient.

In the case of high-performance catalysts for VAM preparation, the STY of which is significantly above 700 g of VAM/l of catalyst×h, the heat of reaction formed is significantly higher, with the consequence that the removal of heat in the steam/water cooling medium, even with the abovementioned measures for increasing the cycle gas velocity, is too slow. The consequences are that there is not just increased occurrence of local temperature increases (hotspots) in the reactor and an associated reduction in ethylene selectivity, but also shortened catalyst service lives and higher by-product formation overall.

EP 1033167 A2 discloses a tube bundle reactor with graduated internal diameter, wherein the tubes in the region of the inlet of the reaction mixture have a smaller diameter than in the region of the outlet of the reaction mixture. The document advises against a general reduction in the diameter of the tubes of a tube bundle reactor, since the manufacturing costs of the reactor (more tubes) would thus increase and the expenditure associated with filling them would rise.

SUMMARY OF THE INVENTION

It was an object of the invention to improve the process for preparing vinyl acetate monomer by reacting ethylene with acetic acid and oxygen in a heterogeneously catalysed, continuous gas phase process to the effect that high-performance catalysts with a space-time yield (STY) of more than 700 g of VAM/l of catalyst×hour can be used, with avoidance of local temperature increases (hotspots) and associated reduction in ethylene selectivity.

DETAILED DESCRIPTION OF THE INVENTION

Figure 1:
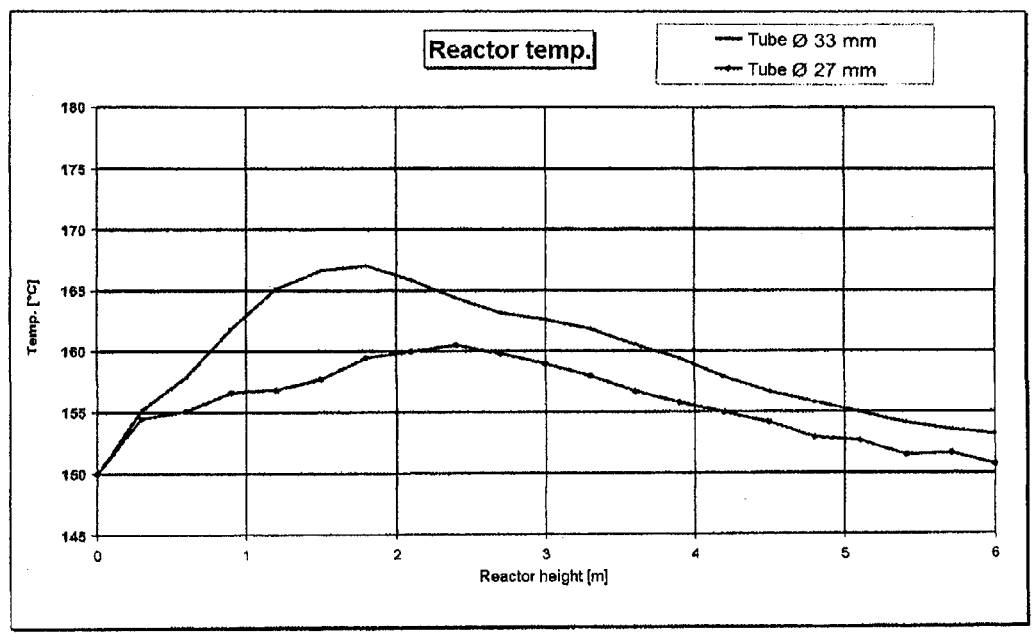
FIG. 1 shows a plot of reactor temperature vs. reactor height after 300 hours in a process according to the invention using a reactor with a 27 mm diameter tube, compared with that of a prior art process using a reactor with a 33 mm diameter tube.

The invention provides a process for preparing vinyl acetate monomer (VAM) by reacting ethylene with acetic acid and oxygen in a fixed bed tube bundle reactor in a heterogeneously catalysed, continuous gas phase process, characterized in that a high-performance catalyst with a space-time yield of >700 g of VAM/l of catalyst×hour is used for catalysis, and in that the fixed bed tube bundle reactor comprises tubes with a ratio of inner surface area to volume of $\geq 130$ m$^{-1}$.

The fixed bed tube bundle reactors used to prepare vinyl acetate monomer consist generally of a cylindrical vessel in which a multitude of cylindrical tubes (the tube bundle) are arranged vertically. The tubes are arranged tightly packed in the bundle. Typically, a fixed bed tube bundle reactor for industrial scale use comprises 2000 to 6000 tubes. In general, the distance between the tubes, i.e. between the central internal axes of the tubes, is 30 to 40 mm. A water/steam mixture as a heat exchange medium flows through the interstices between the tubes themselves, and the tubes and the vessel, for cooling.

The invention further provides an apparatus for performing the process according to the invention, comprising a fixed bed tube bundle reactor with cylindrical tubes with a ratio of inner surface area to volume of $\geq 130$ m$^{-1}$.

Useful reactors for industrial scale use are fixed bed tube bundle reactors with a height of several meters, i.e. generally a tube length of 4 to 7 m. The tubes are steel tubes with a wall thickness of generally 1 to 3 mm. According to the invention, the dimensions of the tubes are such that the ratio thereof of surface area (in the tube interior) to tube volume is $\geq 130$ m$^{-1}$, preferably 130 to 160 m$^{-1}$. The internal diameter of the tubes is preferably constant over their entire length.

It was found that, compared to the conventional A:V ratio of about 100 to 120 m$^{-1}$, especially at a surface area/volume ratio of 130 to 160 m$^{-1}$, improvements with regard to heat removal of >30% are achievable. Even more significant removal of heat is achievable with significantly smaller tube diameters, but the tube filling then begins to become uneconomic, or the ever narrower tubes result, in the course of filling, in considerable bridge and gap formations of the catalyst bodies, particularly at the walls. Although this can be counteracted by a reduction in the catalyst particle size, this in turn leads to a reduction in the void volume and hence to a considerable rise in the pressure difference.

For catalysis, the tubes are filled in a known manner with particulate high-performance catalysts with a space-time yield of >700 g of VAM/l of catalyst×hour, preferably 800 to 1500 g of VAM/l of catalyst×hour, more preferably 900 to 1500 g of VAM/l of catalyst×hour. They are generally supported catalysts based on an inert, inorganic support material such as titanium oxides, silicon oxides, aluminium oxides, which are coated with a palladium compound in combination with alkali metal salts, and may additionally be doped with gold, rhodium or cadmium. The supported catalysts may be present in the form of spheres, cylinders or rings, the dimensions thereof being matched to the tubes used, and they generally have lengths and widths of 3 to 10 mm and diameters of 3 to 6 mm.

The most noticeable improvement in the inventive procedure was the significant increase in ethylene selectivity, and the parallel significant rise in space-time yield (STY). The oxygen selectivity also improved noticeably. Moreover, the values in the tables show that it was possible to employ almost 10% less condensate circulation. Thus, over and above the gain in selectivity and STY, it is also possible to achieve a power saving in the condensate circulation pumps.

EXAMPLE

The thermal reaction profile was compared in two tubular reactors equipped with tubes with a diameter of 33 mm (comparative) or tubes with a diameter of 27 mm (inventive).

A) A reactor with four tubes (length 6.30 m, internal diameter 33 mm; A/V=120 m$^{-1}$); cooling medium: water/steam with a condensate circulation of 1300 kg/h; external heat removal via a steam drum. One tube equipped with a temperature measurement chain, one measurement point every 20 cm.

B) A reactor with 7 tubes (length 6.30 m, internal diameter 27 mm; A/V=148 m$^{-1}$), cooling medium: water/steam with a condensate circulation of 1240 kg/h; external heat removal via a steam drum. Two tubes equipped with a temperature measurement chain, one measurement point every 20 cm.

Both reactors were filled with a VAM catalyst, KL 7900 SH from KataLeuna, Germany (Pd 1.5% by weight; Au 1% by weight). Since the results, in the case of use of the space-time yield (STY=g of VAM/l of catalyst×hour), relate to 1 liter of catalyst, the greater amount of catalyst in the 7-tube reactor is unimportant.

In a VAM pilot plant with the two reactors A and B, identical catalysts were tested under identical reaction conditions.

Figure 2:
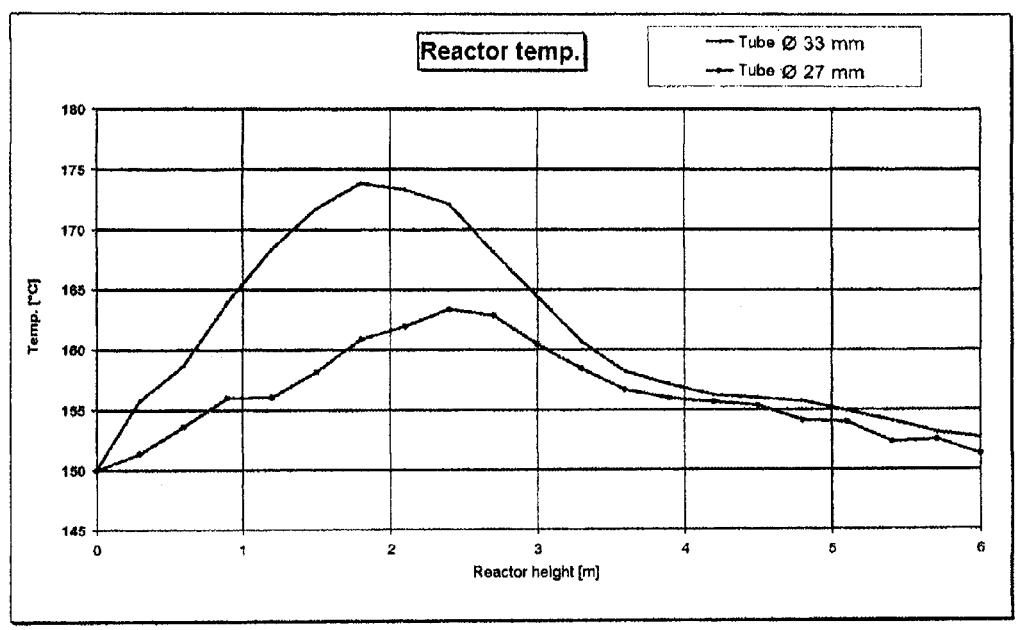
FIG. 2 shows a plot analogous to that of FIG. 1, taken after 400 hours reaction time.
Figure 3:
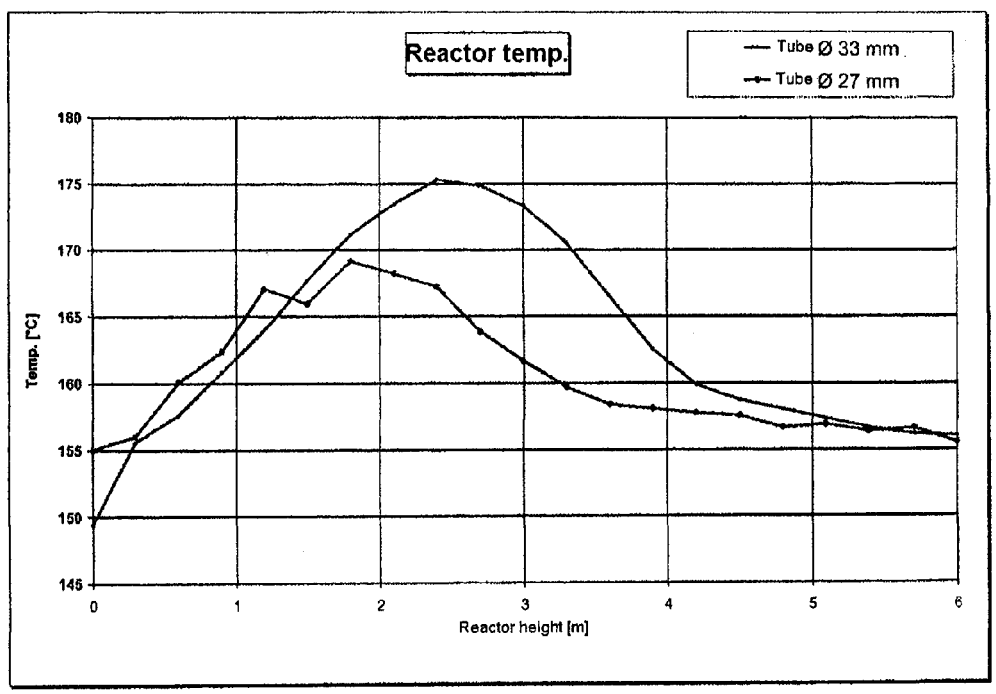
FIG. 3 shows a plot analogous to that of FIG. 1, taken after 1000 hours reaction time.
Figure 4:
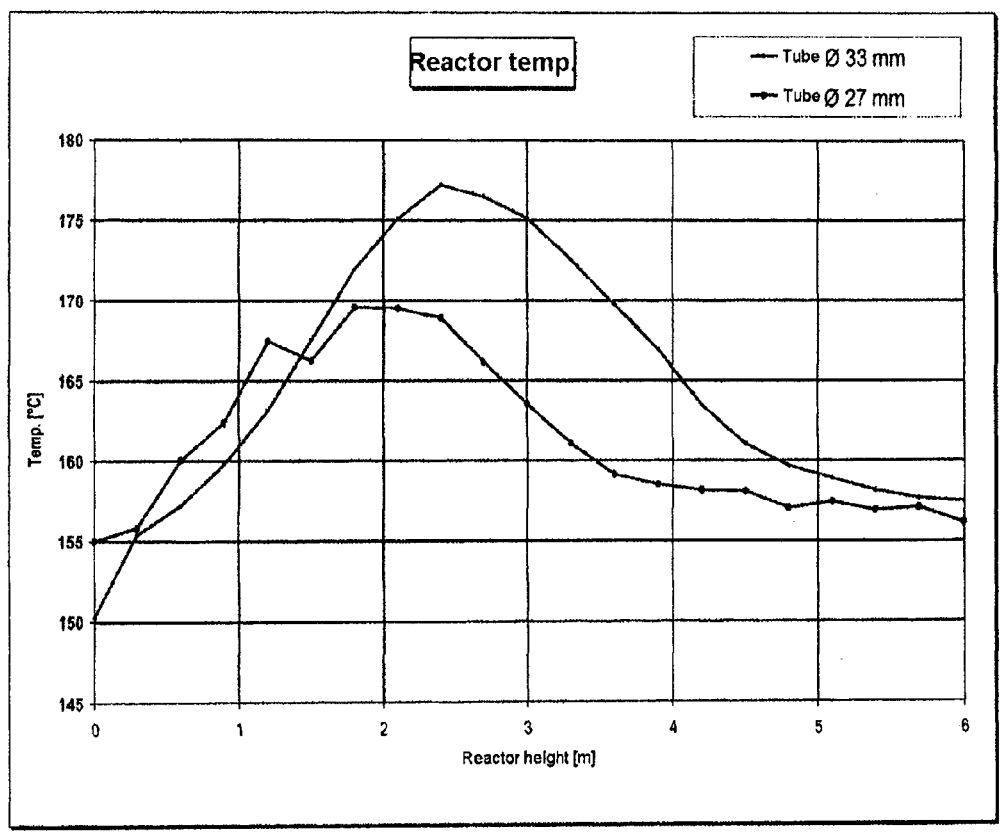
FIG. 4 shows a plot analogous to that of FIG. 1, taken after 1500 hours reaction time.

The reaction conditions, space-time yield and selectivity are shown in Table 1 (after 300 h), Table 2 (after 400 h), Table 3 (after 1000 h) and Table 4 (after 1500 h). The temperature profile in the reactors is shown in FIG. 1 (after 300 h), FIG. 2 (after 400 h), FIG. 3 (after 1000 h) and FIG. 4 (after 1500 h).

As early as after 300 hours, a significantly improved temperature profile was found in the inventive procedure. The temperature difference between the comparative reactor and the reactor equipped in accordance with the invention was up to more than 10° C., which became even more clear after an operating time of 400 h. It was thus possible to obtain an increase in the ethylene selectivity of more than 1% in the initial period (300 to 400 h). The advantages became even more clear with increasing experiment time, in spite of another increase in the amount of condensate circulated in the reactor with large tubes, but homogeneous circulation in the case of the 27 mm tubes, i.e. less cooling in the reactor with 27 mm tubes, the ethylene selectivity in the latter improved by 2%.

TABLE 1

(Conditions and performance after 300 hours)

| | Tube diameter | |
|---|---|---|
| | 33 mm | 27 mm |
| Cycle gas pressure ($p_e$) | 8.5 | 8.5 |
| AcOH (%) | 12.0 | 11.5 |
| $C_2H_4$ (%) | 65 | 65 |
| Temperature (° C.) | 150 | 150 |
| $O_2$ (%) | 6.8 | 6.8 |
| Condensate circulation (kg/h) | 1340 | 1240 |
| GHSV (1/h) (GHSV = Gas Hourly Space Velocity) | 3740 | 3720 |
| STY (kg VAM/l cat × h) | 850 | 850 |
| $C_2H_4$ selectivity | 92.1 | 93.3 |
| $O_2$ selectivity | 65-70 | 75-80 |

TABLE 2

(Conditions and performance after 400 hours)

| | Tube diameter | |
|---|---|---|
| | 33 mm | 27 mm |
| Cycle gas pressure ($p_e$) | 8.5 | 8.5 |
| AcOH (%) | 12.3 | 11.5 |
| $C_2H_4$ (%) | 65 | 65 |
| Temperature (° C.) | 150 | 150 |
| $O_2$ (%) | 8.6 | 8.8 |
| Condensate circulation (kg/h) | 1340 | 1240 |
| GHSV (1/h) | 3750 | 3750 |
| STY (kg VAM/l cat × h) | 900 | 935 |
| $C_2H_4$ selectivity | 91.0 | 92.3 |
| $O_2$ selectivity | 65-70 | 75-80 |

TABLE 3

(Conditions and performance after 1000 hours)

| | Tube diameter | |
|---|---|---|
| | 33 mm | 27 mm |
| $C_2H_4$ (%) | 61.3 | 63.1 |
| Temperature (° C.) | 150 | 155 |
| Condensate circulation (kg/h) | 1530 | 1230 |
| GHSV (1/h) | 3660 | 3820 |
| STY (kg VAM/l cat × h) | 920 | 980 |
| $C_2H_4$ selectivity | 90.9 | 93.3 |
| $O_2$ selectivity | 55-60 | 65-70 |

TABLE 4

(Conditions and performance after 1500 hours)

| | Tube diameter | |
|---|---|---|
| | 33 mm | 27 mm |
| $C_2H_4$ (%) | 61.0 | 62.0 |
| Temperature (° C.) | 150 | 155 |
| Condensate circulation (kg/h) | 1750 | 1260 |
| GHSV (1/h) | 3600 | 3800 |
| STY (kg VAM/l cat × h) | 930 | 980 |
| $C_2H_4$ selectivity | 91.4 | 93.4 |
| $O_2$ selectivity | 60-65 | 70-75 |

The invention claimed is:

1. A process for preparing vinyl acetate monomer (VAM) by reacting ethylene with acetic acid and oxygen in a tube bundle reactor in a heterogeneously catalyzed, continuous gas phase process, wherein a high-performance catalyst with a space-time yield of more than 700 g of VAM/l of catalyst× hour is used for catalysis, and wherein the tube bundle reactor comprises tubes with a ratio of inner surface area to volume of $\geq 130$ m$^{-1}$.

2. The process according to claim 1, wherein the ratio of inner surface area to volume is from 130 to 160 m$^{-1}$.

3. The process according to claim 1, wherein the tube bundle reactor comprises tubes with a tube length of 4 meters to 7 meters.

4. The process according to claim 1, wherein a water/steam mixture as a heat exchange medium flows through the tube bundle reactor for cooling.

5. The process according to claim 2, wherein the tube bundle reactor comprises tubes with a tube length of 4 meters to 7 meters.

6. The process according to claim 2, wherein a water/steam mixture as a heat exchange medium flows through the tube bundle reactor for cooling.

7. The process according to claim 3, wherein a water/steam mixture as a heat exchange medium flows through the tube bundle reactor for cooling.

8. The process according to claim 5, wherein a water/steam mixture as a heat exchange medium flows through the tube bundle reactor for cooling.

* * * * *